United States Patent [19]

Cullen et al.

[11] Patent Number: 4,992,735

[45] Date of Patent: Feb. 12, 1991

[54] SYSTEM AND METHOD FOR INSPECTING METALLIC PLUGS IN HEAT EXCHANGER TUBES USING A RADIALLY EXTENDIBLE PROBE

[75] Inventors: William K. Cullen, Penn Hills; Charles H. Roth, Jr., N. Huntingdon; Lee W. Burtner; Francis X. Gradich, both of Elizabeth Township, Allegheny County; David A. Chizmar, Washington Township, Westmoreland County; Lawrence Galata, North Huntingdon, all of Pa.

[73] Assignee: Westinghouse Electric Corp., Pittsburgh, Pa.

[21] Appl. No.: 387,997

[22] Filed: Aug. 1, 1989

[51] Int. Cl.⁵ .................... G01N 27/90; G01R 33/12
[52] U.S. Cl. ........................................ 324/220; 33/302
[58] Field of Search ................ 324/219–221, 324/226, 227, 234, 236, 237, 238, 239, 240; 33/302; 73/623

[56] References Cited

U.S. PATENT DOCUMENTS

| | | | |
|---|---|---|---|
| 3,883,879 | 5/1975 | Kettering | 73/620 X |
| 3,931,571 | 1/1976 | Hocking et al. | 324/236 |
| 4,139,822 | 2/1979 | Urich et al. | 324/219 |
| 4,304,134 | 12/1981 | Rouse et al. | 324/220 X |
| 4,412,177 | 10/1983 | Petrini et al. | 324/219 X |
| 4,441,078 | 4/1984 | Lecomte | 324/219 |
| 4,447,777 | 5/1984 | Sharp et al. | 324/220 |
| 4,625,165 | 11/1986 | Rothstein | 324/220 |
| 4,629,984 | 12/1986 | Scalese | 324/219 X |
| 4,851,773 | 7/1989 | Rothstein | 324/220 |

Primary Examiner—Reinhard J. Eisenzopf
Assistant Examiner—Warren S. Edmonds
Attorney, Agent, or Firm—W. S. Stevens

[57] ABSTRACT

An apparatus and a method for remotely inspecting the interior walls of a cavity having a circular cross section that varies in diameter, such as the interior of a hollow tube plug. The apparatus has an eddy current probe head having a distal and proximal end, wherein the distal end engages the cavity walls, an elongated support assembly connected to the proximal end of the probe that is insertable within the cavity, a radial extender mechanism for radially extending and withdrawing the distal end of the probe with respect to the longitudinal axis of the support assembly, and a probe driving and delivery system for inserting the support assembly into the cavity and helically moving the probe head to inspect the cavity walls for discontinuities. In the method of the invention, the radial extender mechanism radially retracts the probe head within the support assembly when it is inserted through the cavity prior to the inspection operation in order to avoid mechanical interference, and then radially extends the probe head into engagement with the cavity walls. The probe driving and delivery system then helically moves the probe head across the cavity walls to scan the walls for discontinuities that indicate cracks.

36 Claims, 6 Drawing Sheets

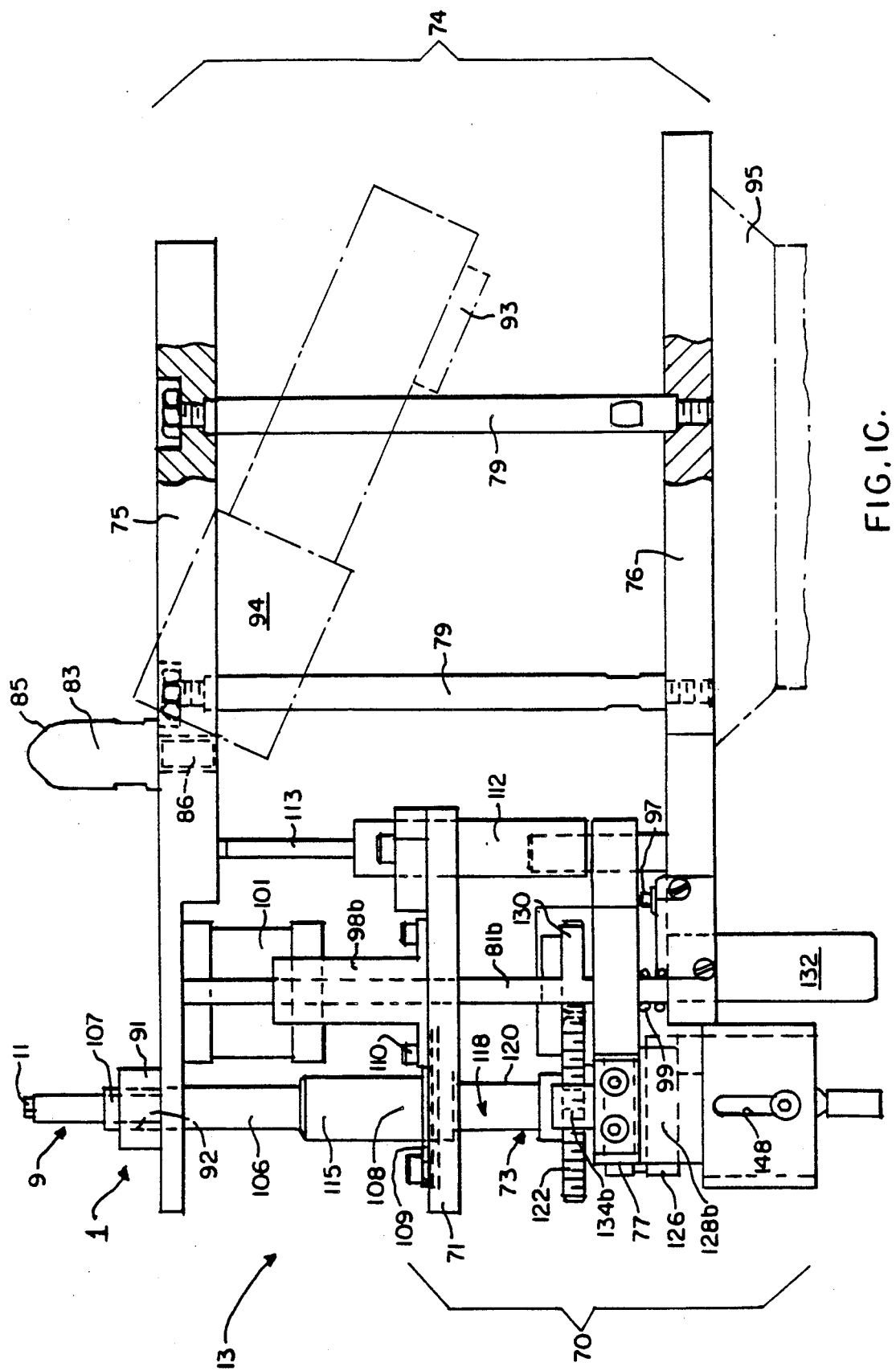
FIG. IC.

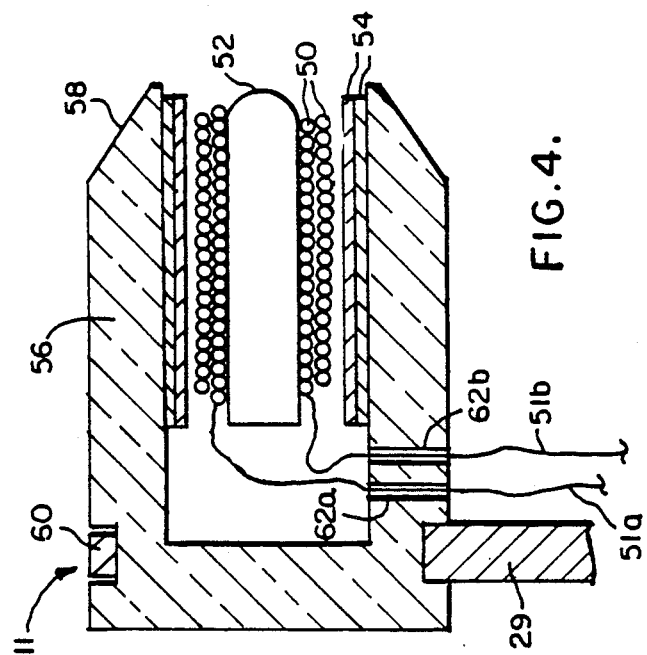
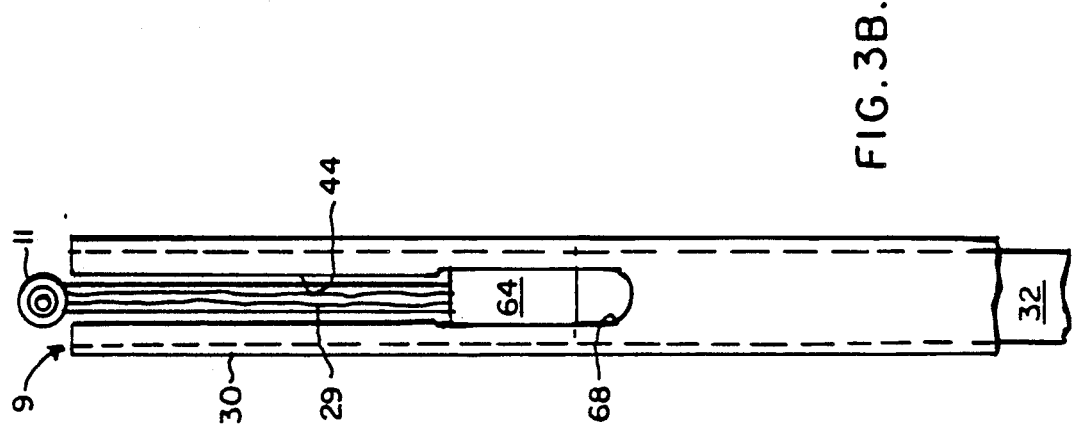
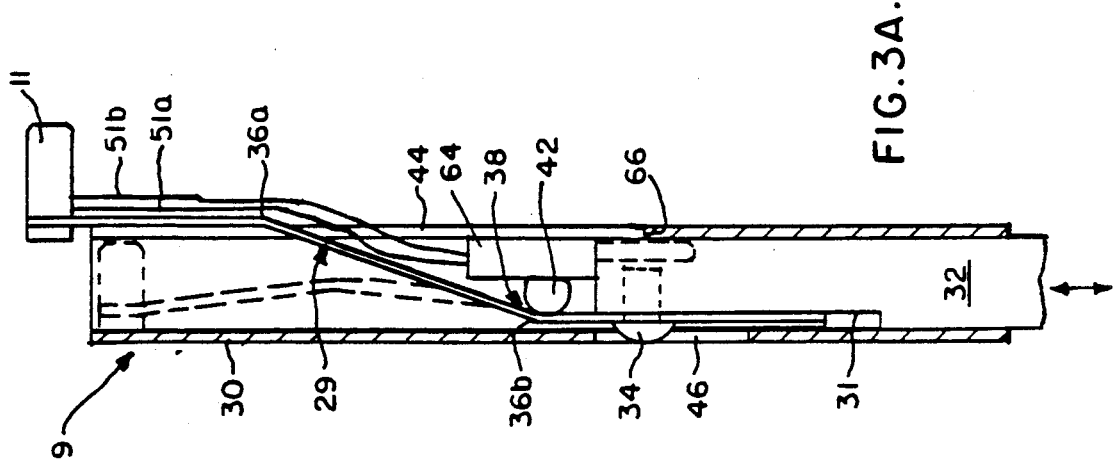

SYSTEM AND METHOD FOR INSPECTING METALLIC PLUGS IN HEAT EXCHANGER TUBES USING A RADIALLY EXTENDIBLE PROBE

BACKGROUND OF THE INVENTION

This invention generally relates to a system and method for detecting flaws in the interior walls of a cavity, and is specifically concerned with inspecting the interiors of the hollow metallic plugs that are presently used to seal defective heat exchanger tubes in nuclear steam generators.

Systems for inspecting the interiors of the heat exchanger tubes used in nuclear steam generators are known in the prior art. Such systems typically employ one or more eddy current probes to detect the presence or absence of discontinuities in the tube walls created by cracks or pits in these walls. In such systems, an eddy current probe in the form of a coil whose axis of rotation is oriented along the longitudinal axis of the tube is moved throughout the tube while an alternating current is conducted through the coil. The alternating current causes the coil to emanate a time-varying magnetic field which in turn induces eddy currents in the inner walls of the tube as the coil is moved axially. Because the eddy currents create a magnetic field which is opposite in polarity to the time-varying magnetic field emanated by the probe coil, the eddy currents generated in the tube apply a measurable impedance to the alternating current that fluctuates through the coil. This impedance is highest when the metal conducting the eddy current is free from discontinuities such as cracks or pits or other imperfections in the metal. However, when such imperfections are present, the eddy currents induced in the metallic walls of the tube are subjected to a resistance, which in turn causes the electromagnetic field generated by the eddy currents to impede the time-varying magnetic field generated by the coil to a lesser extent. This reduction in impedance is usually measured by means of an AC bridge circuit connected between the input and the output of the probe coil.

While such axially-oriented eddy current probe coils were capable of detecting the presence or absence of cracks or other discontinuities in the tube walls, they were not readily capable of determining either the orientation of the crack or its precise location with respect to the longitudinal axis of the tube. To address these shortcomings, surface-riding "pancake" type eddy current coil probe systems were developed. In such systems, the probe coil is made very small (about two mm in diameter or less), and is helically moved along the axis of the tube in wiping engagement of the inner wall of the tube. Because such probes are moved in accordance with a known screw pitch, cylindrical coordinates may easily be assigned to every location on the walls that the pancake probe assumes during its helical motion. Such probes are able to pinpoint the location of cracks and other flaws in the tube wall, and to create a fine-resolution picture of the orientation and extent of the crack or other flaw. Such a pancake-type eddy current probe is used in the invention disclosed in U.S. Pat. application Ser. No. 079,860 filed July 30, 1987, by Michael J. Metala and entitled "Apparatus and Method For Providing a Combined Ultrasonic and Eddy Current Inspection of a Metallic Body" and assigned to the Westinghouse Electric Corporation.

While such surface-riding pancake-type eddy current coils represent a significant advance in the art, the physical configuration of such probes has thus far limited their application to relatively smooth-walled cylindrical cavities such as the interiors of heat exchanger tubes. The structural configuration of all known surface-riding coils would render them difficult if not impossible to use within a cavity characterized by step-wise, varying diameters such as the interior of one of the hollow metallic plugs used to seal off a defective heat exchanger tube from the primary system of the steam generator. Such plugs comprise a tube shell having a closed end, an open end and a generally cylindrical interior which has been radially expanded by means of a cork-shaped expander element that has been forcefully drawn from the closed end to the open end of the plug cavity. While the expander elements in such plugs include a centrally disposed bore that leads to the upper section of the plug interior, no known surface-riding pancake-type eddy current coil is capable of being inserted through this relatively narrow bore and engaged against and helically moved around the interior walls of the upper section of such a plug. This is an unfortunate limitation, as the applicants have observed that the upper wall section of such plugs are susceptible to stress corrosion cracking as a result of the substantial tensile stresses applied to the walls of the plug shell in the upper region by the cork-shaped expander element when it is drawn from the closed to the open end of the plug shell.

Clearly, what is needed is a system and method for inspecting the interiors of the tube plugs used in nuclear steam generators so that these plugs may be replaced or repaired in the event of stress corrosion cracking. Ideally, such an inspection system should be capable of quickly, accurately, and reliably scanning all parts of the upper interior walls of a plug shell above the expander element in order to determine not only the presence of any and all flaws, but their extent and orientation within the plug shell. Finally, such an inspection system should be positionable with known robotic systems in order to avoid exposing maintenance personnel to potentially harmful radiation.

SUMMARY OF THE INVENTION

Generally speaking, the invention is both an apparatus and a method for remotely inspecting the interior walls of a cavity within an electrically conductive material that has a varying diameter, such as the hollow interior of a metallic plug that has been used to seal off a heat exchanger tube in a steam generator. The apparatus generally comprises an eddy current probe head having a distal end for engaging the cavity walls, and a proximal end, and elongated support assembly connected to the proximal end of the probe that is insertable within the cavity, a radial extender mechanism for radially extending and retracting the distal end of the probe with respect to the longitudinal axis of the support assembly so that the probe can negotiate step-wise changes in the diameter of the cavity without mechanical interference, and a probe driving and delivery assembly for inserting the support assembly into the cavity and helically moving the probe head against the cavity walls to scan them for defects. The support assembly includes a tubular housing, and a bent, leaf-spring support member that is connected to the probe head at its distal end, and disposed within the housing. The radial extender mechanism includes a push-rod means connected to the proximal end of the support member for axially moving within the tubular housing.

The radial extender mechanism may further include a cam mounted within the tubular housing that engages a bent portion of the leaf-spring member to radially flex it upon axial movement by the push-rod. A pneumatic cylinder may be used to drive the push-rod in order to provide the axial movement that flexes the leaf-spring support member into a radial extension or retraction which, in turn, is transferred to the probe head.

The probe driving and delivery system may include a drive mechanism that inserts the probe support assembly into a cavity and helically drives the probe head, and a frame onto which the drive mechanism is slidably mounted. The drive mechanism may utilize a screw-threaded member, such as a tube with a screw thread on its outer diameter, to both insert the probe support assembly into the cavity, as well as to helically move the probe head to scan the cavity walls. The drive mechanism preferably further includes an indexing member insertable through the open end of the cavity for locating the axial point within the cavity where there is a step-wise change in diameter. In the preferred embodiment, the indexing member is a tubular member that is insertable through the open end of a plug shell and engageable against the expander element therein to stop the sliding movement of the drive mechanism relative to the frame. A linear variable differential transformer (LVDT) is connected between the drive mechanism and the frame in order to convert the position of the drive mechanism relative to the frame into an indication of where the expander element is with respect to the bottom surface of the plug.

In the method of the invention, the frame of the probe driving and delivery assembly is positioned so that the drive mechanism is aligned beneath the open end of a cavity to be inspected, which may be the hollow interior of a plug used to seal a defective heat exchanger tube in a nuclear steam generator. Next, the tubular indexing member which circumscribes the probe support assembly is extended upwardly into abutment with the bottom end of the expander element by gently sliding the entire drive mechanism upwardly within the frame. The output of the LVDT that is connected between the drive mechanism and the frame is converted into an indication as to the location of the expander element along the longitudinal axis of the plug. The probe head is next inserted up through the open end of the plug and through the relatively narrow bore within the expander element with the probe head in a retracted position in order to avoid mechanical interference. Such insertion is implemented by means of the screw-threaded member of the drive mechanism, which may be a tubular member having a screw thread on its outer diameter. Once this has been accomplished, the radial extender mechanism is used to extend the probe head into wiping engagement with the interior walls of the upper region of the hollow plug, and the screwthreaded member is then used to impart a helical, scanning motion to the probe head. At the termination of the inspection, the probe head is retracted, and the support assembly withdrawn from the plug, and the process repeated with another plug.

BRIEF DESCRIPTION OF THE SEVERAL FIGURES

FIGS. 1B and 1C are partial cross-sectional views of the left side and right side, respectively, of the inspection system illustrated in FIG. 1A.

FIG. 3A is an enlarged, cross-sectional side view of the probe support assembly of the invention.

FIG. 3B is a front view of the support assembly illustrated in FIG. 3A.

FIG. 4 is an enlarged, cross-sectional view of the probe head used in the system of the invention.

DETAILED DESCRIPTION OF THE PREFERRED EMBODIMENT

Figure 1A:
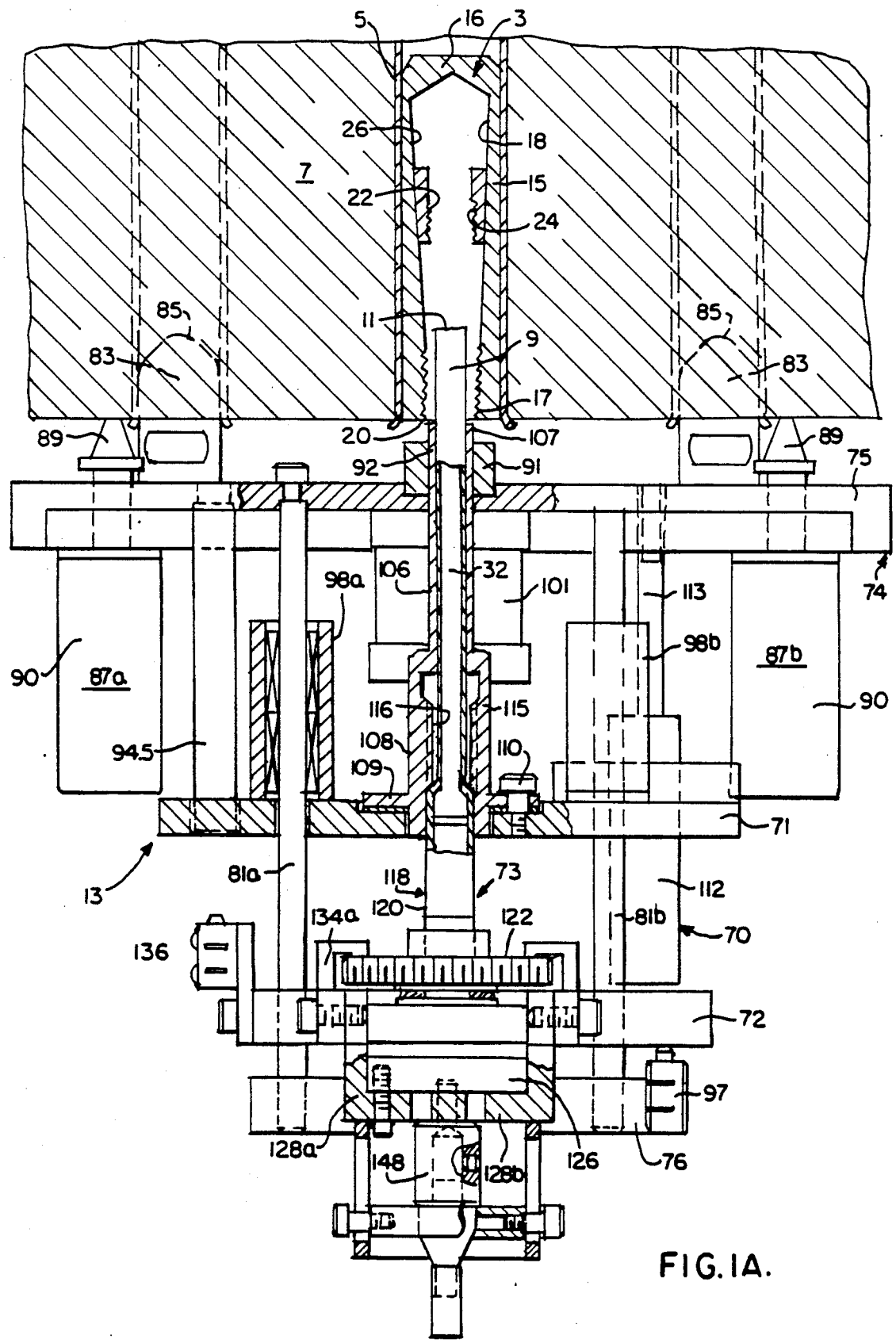
FIG. 1A is a partial cross-sectional front view of the system of the invention as it would appear just prior to the inspection of one of the plugs used to seal off a defective heat exchanger tube in a nuclear steam generator.

With reference now to FIG. 1A, wherein like numerals designate like components throughout all the several figures, the plug inspection system 1 of the invention is particularly useful in inspecting the Inconel ® plugs 3 that are used to seal off the defective heat exchanger tubes 5 whose open ends are mounted in the tubesheet 7 of a nuclear steam generator. To this end, the system 1 generally comprises an eddy current probe support assembly 9 having a radially extendible and retractable probe head 11 at its top end, as well as a probe driving and delivery assembly 13 for both inserting the probe support assembly 9 into the plug 3 and helically moving it so that the probe head 11 scans the inner wall of the plug 3 to detect any cracks or other flaws which may be present therein.

The plugs 3 used to seal off the open ends of such tubes 5 generally comprise a tubular plug shell 15 having a closed end 16 and an open end 17. The closed end 16 extends into the open end of the heat exchanger tube 5 a few centimeters, while the open end 17 of the shell 15 is situated approximately even with the open end 17. As is evident in FIG. 1A, the plug shell 15 is essentially hollow and includes tapered walls 18 which define a tapered interior that becomes progressively narrower from the closed end 16 to the open end 17 of the shell 15. A cork-shaped expander element 22 having a centrally disposed, threaded bore 24 is disposed in the tapered interior of the plug shell 15. Prior to the expansion of the plug 3 into engagement with the inner walls of the heat exchanger tube 5, the upper end of the cork-shaped expander element 22 is positioned adjacent to the closed end 16 of the plug shell 15. After the plug 3 has been inserted into the position illustrated in FIG. 1A, the plug 3 is expanded by means of a special tool (not shown) having a threaded pull rod that engages the threaded bore 24 of the expander element 22 and axially draws it down toward the open end 17 of the plug shell 15. The application of such a pull-down force on the expander element 22 causes it to wedgingly engage the tapered walls 18 of the plug shell 15 and to radially expand the plug 3 into leak tight engagement with the interior walls of the heat exchanger tube 5. Unfortunately, the substantial compressive and tensile forces that the expander element 22 applies to the tapered walls 18 has been found, in some instances, to create tensile stresses in the plug walls that promote the occurrence of stress corrosion cracking, particularly in the section 26 of the tapered walls 18 disposed between the upper end of the expander element 22, and the closed end 16 of the plug shell 15. A primary purpose of the plug inspection system 1 of the invention is to provide an eddy current inspection of this upper section 26 of the walls 18 15 so that the presence of any such cracks or other flaws may be accurately and reliably determined.

Figure 5C:
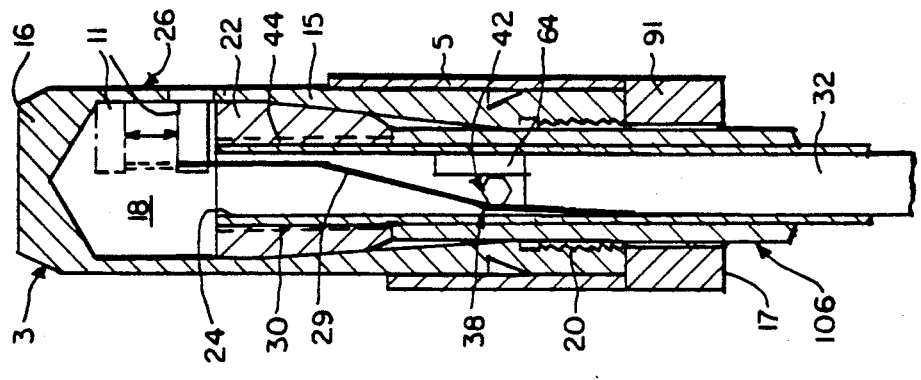
FIG. 5C is a cross-sectional side view of the probe head in a radially extended position within the upper section of a plug as it would appear during an inspection operation.

With reference now to FIGS. 3A and 3B, the eddy current probe support assembly 9 includes a resilient support member 29 preferably formed into a leaf-spring which is contained within a tubular housing 30 whose outer diameter is smaller than the inner diameter of the threaded bore 24 of the expander element 22. The upper end of the leaf-spring support member 29 supports the probe head 11 as shown, while the bottom end of the support member 29 is connected onto a recessed section 31 of a push-rod 32 by means of a screw 34. In its middle, the leaf-spring support member 29 includes upper and lower bent portions 36a and 36b. Bent portion 36b forms a cam surface 38 which is engageable against a rounded cam 42 mounted across the walls of the tubular housing 30 when the push-rod 32 is slidably moved within the housing 30. As is best seen in FIG. 3A, when the push-rod 32 has been pushed up into a position where the cam 42 does not engage the cam surface 38, the leaf-spring support member 29 holds the probe head 11 into a radially extended position which is displaced away from the longitudinal axis of the tubular housing 30. Thus positioned, the probe head 11 can wipingly engage the inner walls of the plug shell 15 when the upper end of the tubular housing 30 is aligned with the upper edge of the expander element 22 (see FIG. 5C). However, when the push-rod 32 is pulled downwardly so that the rounded surface of the cam 42 engages against the cam surface 38, the leaf-spring support member 29 is flexed into the radially retracted and withdrawn position illustrated in phantom. In this retracted position, the probe support assembly 9 may be inserted through the relatively narrow bore 24 in the expander element 22 without mechanical interference.

With reference now to FIGS. 3A and 3B, the front side of the tubular housing 30 includes a probe axis slot 44 with allows the probe head 11 and upper end of the support member 29 to assume the position illustrated in FIG. 3A without mechanical interference. On its back side, the tubular housing 30 includes a mounting screw axis slot 46 which allows the system operator to easily detach the leaf-spring support member 29 from the push-rod 32 in the event that a repair becomes necessary.

With reference now to FIGS. 3A, 3B and FIG. 4, the probe head 11 includes an eddy current probe coil 50 which is preferably made from 50 turns of number 40 copper wire which is 0.003 inches, (0.08 millimeters) in diameter. The ends of the coil 50 terminate in lead wires 51a and 51b as shown. The coil 50 is wound around a 0.031 inch (0.79 millimeter) diameter ferrite core which localizes the magnetic field generated by the coil 50 to a relatively sharp point. To further focus this magnetic field, the exterior of the coil 50 is surrounded by netic-conetic shield walls. These shield walls 54 are in turn contained within a cylindrical cover 56 formed from a self lubricating plastic material such as ultra-high molecular weight polyethylene. The distal end of the cylindrical cover 56 includes a tapered portion 58 to better allow the probe head 11 to follow the contour of a cavity having a variable-diameter. A circular recess 60 is provided opposite from the taper 58 for receiving the end of the leaf-spring support member 29. In the middle of the cover 56 a pair of bores 62a, 6b are provided for conducting the leads 51a and 51b of the probe coil 50 out of the cover. As is best seen in FIG. 3B, these leads 51a, 51b are electrically connected to a terminal connector assembly 64 having pins 66 which are receivable within conductive sockets (not shown) present at the upper end of the push-rod 32. The provision of such a terminal connector 64 greatly facilitates the repair or replacement of a probe head 11. To further facilitate such a repair or replacement operation, the bottom end of the probe access slot 44 includes a widened portion 68 in the vicinity of the terminal connector 64.

Figure 1B:
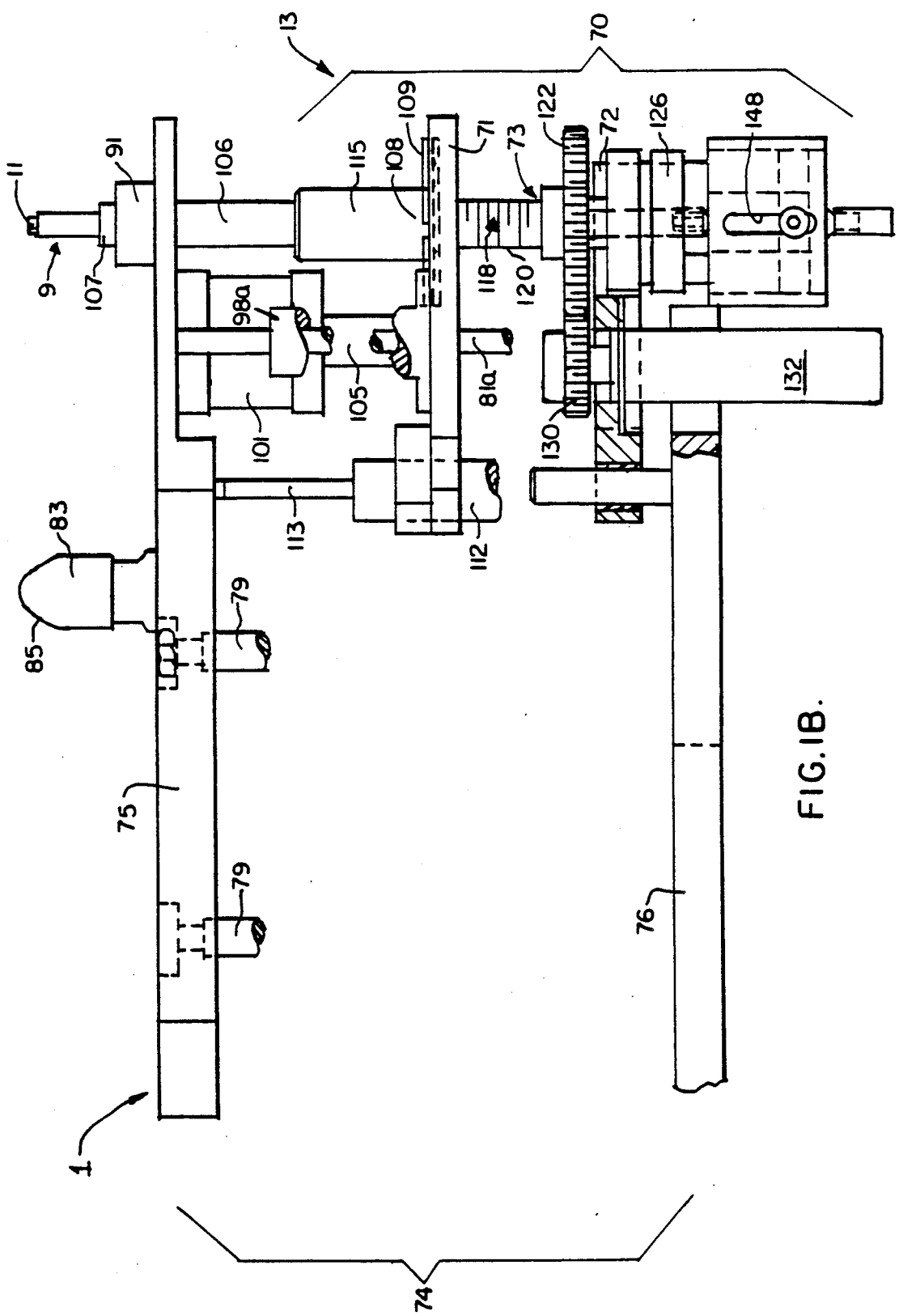

With reference again to FIG. 1A, and further to FIGS. 1B and 1C, the probe driving and delivery assembly 13 is generally formed from a drive mechanism 70 having an indicator table 71, drive table 72, and drive train 73, and a support frame 74 provided with an upper plate 75 and a lower plate 76 interconnected by means of support pins 79. The support frame 74 further includes, at its front end, a pair of guide rods 81a and 81d onto which the indicator and drive tables 71,72 are slidably mounted.

The upper plate 75 of the support frame 74 includes a pair of guide pins 83 having tapered ends 85 which are insertable within the open ends of heat exchanger tubes which flank a tube 5 having a plug 3 being serviced. The bottom end of each of these guide pins 83 includes a screw shaft 86 which allows it to be threadedly mounted in a bore present within the upper plate 75. The guide pins 83 advantageously help to facilitate proper alignment between the probe support assembly 9 connected to the drive train 73 of the mechanism 70 and the open end of a plug 3. The upper plate 75 further includes two pairs of opposing linear variable differential transformers (LVDTs) 87a and 87b. Each of these LVDTs includes a spring loaded feeler rod 89 slidably movable within a transformer body 90. In operation, the two opposing LVDTs 87a and 87b inform the operator of the plug inspection system 1 whether or not the upper plate 75 of the support frame 74 is in a close, parallel position with respect to the underside of the tubesheet 7. Such information is important, as a non-parallel orientation between the upper plate 75 and the underside of the tubesheet 7 could cause damaging mechanical interference to occur between the bore 24 of the expander element 22 and the upper end of the probe support assembly 9 during the insertion operation. A circular stand-off 91 is provided in the front, central portion of the upper plate 75. In operation, the stand-off 91 is received within the flared, open end of the heat exchanger tube 5 in placed into abutment against the underside of the plug 3 to help align the probe support assembly 9 with the threaded bore 24 of an expander element 22. The stand-off 91 includes a centrally located bore 92 for conducting both the upper end of the rod-like probe support assembly 9 as well as the indexing tube 106 that surrounds the support assembly 9. Disposed on the underside of the upper plate 75 is a camera bracket 93 for supporting a closed circuit television camera 94 whose lens faces the stand-off 91 and the upper end of the probe support assembly 9 to assist the system operator in properly aligning these components with the underside of a plug 3. Finally, an upper limit pin 94.5 is disposed on the underside of the upper plate 75 in opposition to an upper limit switch 136. The pin 94.5 is approximately the length of the interior of the plug shell for a purpose that will be discussed later. The lower plate 76 of the support frame 74 includes, on its under side, a coupling 95 (shown in phantom) for a robotic manipulating device, which may be the robotically operated service arm (ROSA) developed and patented by the Westinghouse Electric Corporation. On its upper side, the lower plate 76 includes a lower limit switch 97 for informing the system operator that the drive mechanism 70 has slid to its lowest point within the support frame 74.

Turning now to the drive mechanism 70, a pair of linear bearings 98a and 98b are mounted onto the indexing table 71 which slidably receive the previously mentioned guide rods 81a and 81b connected between the upper and lower plates 75, 76 of the support frame 74. Since the drive table 72 has bores which slidably receive the guide rods 81a and 81b, and since the indexing and drive tables 71 and 72 are coupled together by the drive train 73, the entire drive mechanism 70 is vertically movable within the frame 74. The drive mechanism 70 is positively moved along the guide rods 81a and 81b by the coaction of a pair of compression springs 99 coiled around the bottom ends of the guide rods 81a and 81b, and a pneumatic cylinder 101 having a rod 105 that is connected between the underside of the upper plate 75, and the upper side of the indexing table 71. The coil springs 99a, 99b exert a sufficient amount of compressive force between the lower plate 76 and the underside of the drive table 72 to lift the entire drive mechanism 70 into its upwardmost position within the support frame 74. As will be discussed in more detail hereinafter, during the initial stages of the operation of the plug inspection system 1, the rod 105 of the pneumatic cylinder 101 is actuated to push the two tables 71 and 72 of the drive mechanism into a lower most position within the support frame 74, and then is gradually de-actuated so that the coil spring 3 99a and 99b gently lift the drive mechanism 70, and the probe support assembly 9 connected thereto, into the open end 17 of the plug shell 15 and through the threaded bore 24 of the expander element 22.

The drive mechanism 70 further includes the previously mentioned indexing tube 106 and an LVDT 112 which coact to inform the system operator of the relative position of the expander element 22 along the longitudinal axis of the plug 3. To this end, the indexing tube 106 includes an upper end whose diameter is small enough to extend through the open end 17 of the plug shell 15, but large enough so that it engages against the bottom end of the expander element 22. The lower end 108 of the indexing tube 106 includes a mounting flange that is secured to the indexing table 71 by means of step bolts 110 that pass through oversized bores (not shown) in the flange. These step bolts 110 prevent the flange 109 from moving vertically with respect to the indexing table 71, but do afford a small degree of lateral movement between the bottom surface of the flange 109, and the table 71. To facilitate such lateral movement, a washer 111 formed from a self lubricating plastic such a Delrin ® is disposed between the flange 109 and the indexing table 71. The lateral compliance afforded by the step bolts 110, the over-sized bores in the flange 109, and washer 111 advantageously allows the indexing tube 106 align itself with the open end 17 of the plug shell 15 despite misalignments which may have occurred due to an despite misalignments which may have occurred due to an imperfect positioning of the system 1 by a robotic arm.

An indexing LVDT 112 having a slidable rod 113 is connected between the underside of the upper plate 75 of the support frame 74, and the top of the indexing table 71. Because the axial length of the expander element 22 is known prior to the maintenance operation, the system operator is able to infer with precision the transition point between the upper edge of the expander element 22, and the upper section 26 of the tapered walls 18 of the plug shell 15 from the output of the indexing LVDT 112, which directly informs the system operator the extent to which the indexing table 71 can rise with respect to the upper plate 75 before the bottom end of the indexing tube 106 engages the bottom surface of the expander element 22.

As is readily apparent in FIG. 1A, the lower end 108 of the indexing tube 106 includes an enlarged portion 115 which is circumscribed in its interior by an internal diameter thread 116. A drive tube 118 extending upwardly from the drive table 72 includes an external diameter thread 120 that mates with the internal diameter thread 116 of the indexing tube 106. As will become apparent hereinafter, the cooperation between the external diameter thread 120 of the drive tube 118 and the internal diameter thread 116 of the indexing tube 106 not only extends and retracts the upper end of the probe support assembly 9 into the open end of the plug 3; it further serves to helically move the probe head 11 mounted on the support assembly 9 during the inspection operation.

Figure 2:
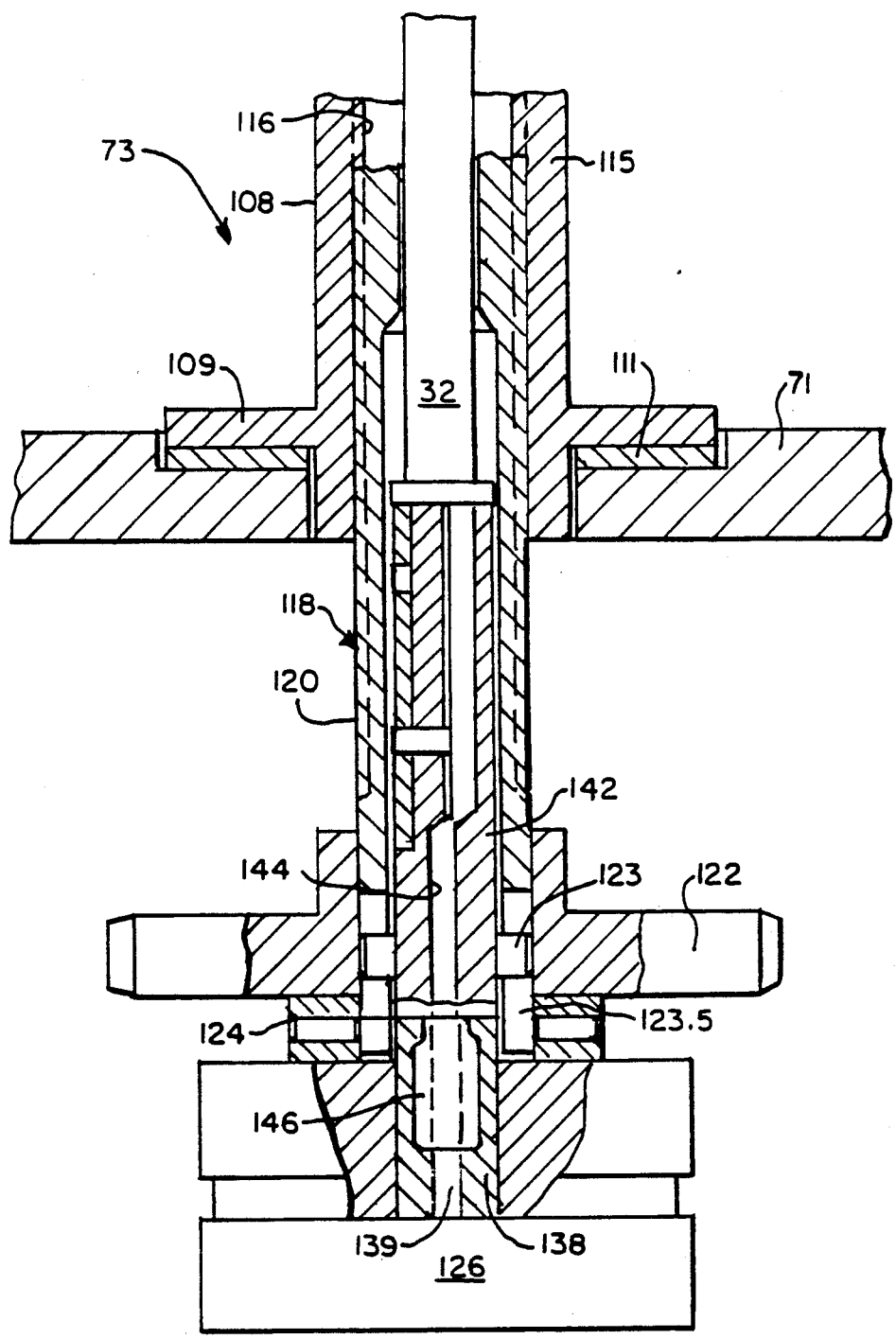
FIG. 2 is an enlargement of the circled section of FIG. 1A, illustrating details of the drive mechanism and radial extender mechanism of the inspection system.

The bottom end of the drive tube 118 is connected at its bottom to a spur gear 122. (see FIG. 2). A pin 123 couples the drive tube 118 to a linkage which is ultimately connected to the push-rod 32 of the probe support assembly so that the drive tube 118 also rotates the probe support assembly 9. Directly beneath the spur gear 122 is a thrust bearing which prevents the bottom of the gear 122 from rubbing against a hydraulic cylinder 126 having a stroke of approximately the drive table 72 by means of opposing support brackets 128a and 128b. A drive gear 130 connected to the output of a reversible motor 132 meshes with the spur gear 122 and drives it either clockwise or counterclockwise, depending upon the polarity of the electricity conducted to the motor 132. Additionally, pair of opposing hold-down brackets 134a and 134b are connected onto the drive table 72 that over-hang and hence capture the outer edge of the spur gear 122 to ensure that it will not separate and rise over the drive table 72 in response to reactive forces generated by the cylinder 126. Finally, an upper limit switch 136 is provided on the drive table 72 to switch off the reversible motor 132 when the probe head 11 has reached the closed end 16 of the plug shell 15. FIG. 2 illustrates in detail the mechanical relationships between the cylinder 126, used to actuate the radial extender mechanism, and the push bar 32 of this mechanism. Specifically, the cylinder 126 has an actuating rod 138 which includes a centrally disposed bore 139. This bore 139 conducts wires (not shown) which are ultimately conducted to the connector assembly 64 of the probe support assembly 9, and from thence through the coil leads 51a and 51b of the probe head 11.

A connecting member 142 interconnects the rod 138 of the cylinder 126 with the push rod 32 of the radial extender mechanism of the probe support assembly 9. Like the previously discussed rod 138 of the cylinder 126, this connecting member 142 includes a bore 144 for conducting electrical wires to the probe head 11. The lower end of the connecting member 142 has a threaded end 146 which mates with a threaded bore provided on the upper end of the rod 138. The upper end of the connecting member 142 is similarly connected to the lower end of the push rod 32. With further reference to FIG. 1A, the wires (not shown) that are conducted through bore 139 and 144 of the rod 138 and connecting member 132 are ultimately connected to a slip ring connector 148 to prevent them from becoming twisted and tangled when the spur gear 122 rotates the probe support assembly 9.

In the first step of the operation of the plug inspection system 1, the support frame is manipulated into the position shown in FIG. 1A by a ROSA type robotic arm or similar device. At this juncture, the indexing and drive tables 71, 72 of the drive mechanisms are depressed downwardly by the rod 105 of the pneumatic cylinder 101 so that the compressive force of the springs 99a, 99d coiled around the guide rods 81a and 81b is overcome, which in turn has the effect of withdrawing the upper ends of both the indexing tube 106 and the upper end of the probe support assembly 9 into the position illustrated in FIG. 1A. The system operator then manipulates the top edge of the stand-off 91 into abutment with the bottom edge of the open end 17 of the plug shell 15 into the position illustrated in FIG. 5A. All during this step, it should be noted that the length of the housing 30 of the probe support assembly 9 has been dimensioned so that its top end rises above the upper end of the indexing tube 106 by a distance d1, which corresponds to the length d2 of the expander element 22. If the opposing pairs of LVDTs 87a and 87b that are situated on the top plate 75 of the support frame 74 indicate that the upper plate 75 is in parallel relationship with respect to the bottom of the tubesheet 7, the system operator then actuates the cylinder 101 to relax the pushing action of the rod 105 against the indexing table 71, which in turn allows the compression springs 99a and 99b to gently elevate the indexing table 71 and drive table 72 until the top end of the indexing tube 106 extends completely through the open end 17 of the plug shell 15 against the bottom surface of the expander element 22 into the position illustrated in FIG. 5B. Such positioning of the indexing tube 106 brings the top end of the probe support assembly 9 even with the top edge of the expander element 22 as shown. The resulting distance between the underside of the upper plate 75 of the support frame 74 and the upper surface of the indexing table 71 is next sensed by the indexing LVDT 112. From this information, the system operator determines the distance between the bottom end of the expander element 22 and the bottom edge of the plug shell 3. This information can tell the operator if the plug 3 has been sufficiently expanded or if the plug 3 has been over expanded. It can also tell the operator if the expander element 22 has been pushed back, a condition that would require the plug 3 to be removed from service.

All during the time that the indexing tube 106 is being inserted into the open end 17 of the plug shell 15, the pneumatic cylinder 126 of the radial extender mechanism has been actuated to apply a pulling force to the push bar 32.

Figure 5B:
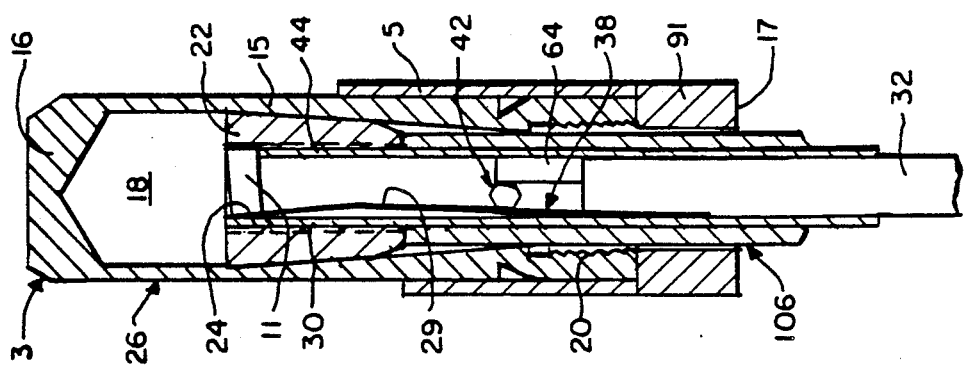
FIGS. 5A and 5B are cross-sectional side views of both the probe support assembly and a plug being inspected by the system of the invention, illustrating how the radial extender mechanism is used to retract the probe head over the support assembly prior to and during its insertion through the narrow bore in the expander element.
Figure 5A:
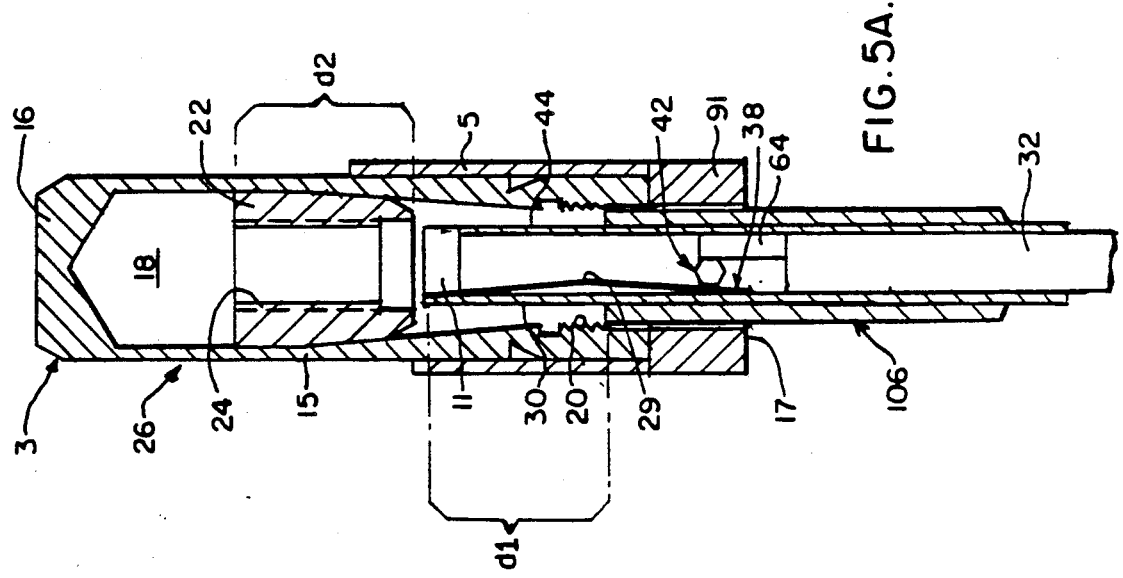

As is best seen in FIGS. 5A and 5B, the application of such a pulling force onto the bar 32 causes the cam surface 38 on the leaf-spring support member 29 to engage the cam 42 that is mounted within the tubular housing 30 of the probe support assembly 9, which has the effect of withdrawing the probe 11 into a radially retracted position. After the indexing tube 106 has been placed into abutment against the bottom end of the expander element 22, the probe head 11 is in the position illustrated in FIG. 5B. At this juncture, the pneumatic cylinder 126 is actuated to push the push-bar 32 of the radial extender mechanism forward toward the plug 3, which in turn slides the cam surface 38 of the leaf-spring support member 29 out of engagement with the cam 42 so that the probe head 11 moves upwardly and radially into the position illustrated in FIG. 5C. The coil 50 within the eddy current probe head 11 is then actuated, and the motor 132 is actuated to turn the spur gear 122 which in turn rotates the drive tube 118 along with the push bar 32 and housing 30 of the probe support assembly 9 through linkage pin 123. As a result of these mechanical actions, the distal, tapered end of the probe head 11 helically sweeps around the inner walls of the upper section 26 of the plug shell 15 in wiping engagement. The scan is completed when the probe head is in near abutment with the closed end 16 of the plug shell 15, as in indicated in phantom at FIG. 5C. At this juncture, the upper limit switch 136 is actuated by the pin 94.5 (shown in FIG. 1A) to shut off the electric motor 132, whereupon the operator actuates the pneumatic cylinder 126 to withdrawn rod 138, which pulls down the push-bar 32 and retracts the probe head 11 back into the housing 30 of the probe support assembly 9. The motor 132 is then actuated in the reverse direction to withdraw the upper end of the probe support assembly 9 back into the position illustrated in FIG. 5B by way of the drive tube 118. The probe support assembly 9 is then withdrawn through the bore 24 of the expander element 22 and out through the open end 17 of the plug shell 15, and the plug inspecting system 1 is then moved to inspect another plug.

We claim:

1. A system for remotely inspecting the interior walls of a cavity within an electrically conductive material, said cavity having a step-wise varying width, comprising:
    an eddy current probe means having a coil means at its distal end for engaging said cavity walls, and a proximal end;
    an elongated support assembly connected to the proximal end of said probe means that is insertable within said cavity, including a tubular housing, and a radial extender means for selectively radially extending the probe means and selectively retracting the distal end of said probe means completely within said housing to avoid mechanical interference between the distal end of said probe means and the step-wise varying widths of said cavity.

2. A system for remotely inspecting the interior walls of a cavity as defined in claim 1, wherein said elongated support assembly includes an elongated support member having a distal end that is connected to the proximal end of the probe means for supporting said probe.

3. A system for remotely inspecting the interior walls of a cavity as defined in claim 2, wherein said elongated support member is resiliently movable with respect to the longitudinal axis of the support assembly.

4. A system for remotely inspecting the interior walls of a cavity as defined in claim 3, wherein said radial extender means includes a cam means engageable against said elongated support member for selectively extending and selectively retracting the distal end of the probe means by flexing said resilient support member.

5. A system for remotely inspecting the interior walls of a cavity as defined in claim 4, wherein said radial extender means includes a push-bar member that is connected to the elongated support member and is movable along the longitudinal axis of said support member.

6. A system for remotely inspecting the interior walls of a cavity as defined in claim 5, wherein said radial extender means includes a pneumatic cylinder means for axially moving said push-bar member and said resilient support member.

7. A system for remotely inspecting the interior walls of a cavity as defined in claim 1, wherein the distance between the distal and proximal ends of the probe means is greater than the maximum variation in the width of said cavity in said conductive material.

8. A system for remotely inspecting the interior walls of a cavity as defined in claim 1, further comprising a probe driving and delivery system for rotating said support assembly so that said probe means scans the interior walls of said cavity.

9. A system for remotely inspecting the interior walls of a cavity as defined in claim 1, wherein said probe means includes a probe coil, a ferrite core circumscribed by the interior of said coil for focusing magnetic fields generated by said coil, and a cover means circumscribing the exterior of said coil.

10. A system for remotely inspecting the interior walls of a cavity within an electrically conductive material having a smaller diameter section that leads into a larger diameter section in a stepwise fashion, comprising;
an eddy current probe means having a coil at its distal end for engaging said cavity walls, and a proximal end;
an elongated support assembly operatively connected to the proximal end of said probe means that is insertable within and withdrawable from said cavity, including a radial extender means for selectively extending and selectively retracting the distal end of said probe means with respect to the longitudinal axis of said support assembly as said probe means is inserted and withdrawn with respect to said cavity to avoid mechanical interference between said probe means and the smaller diameter section of the cavity and a tubular housing having an open end through which said probe means is extended out of and completely retracted into, and
a probe driving and delivery assembly connected to the support assembly for inserting the support assembly into said cavity and moving said probe means over the walls of said cavity.

11. A system as defined in claim 10, wherein said probe driving and delivery assembly includes a drive mechanism that inserts the probe means into the larger diameter section of the cavity and scanningly moves said probe means around the walls of said larger diameter section.

12. A system as defined in claim 11, wherein said probe driving and delivery assembly includes an indexing means for determining the transition point along the axis of rotation of the cavity between the smaller and larger diameter sections of the cavity.

13. A system as defined in claim 12, wherein said indexing means includes an indexing member that is insertable within the cavity.

14. A system as defined in claim 11, wherein said drive mechanism includes means for helically moving the distal end of said probe means around the interior walls of the cavity.

15. A system as defined in claim 14, wherein said helical moving means includes a threaded drive tube means.

16. A system as defined in claim 10, wherein said support assembly includes an elongated, resilient support member having one end connected to the proximal end of the probe means, and said radial extender means includes a push-bar means connected to the other end of the resilient support member for axially moving said support member.

17. A system as defined in claim 16, wherein said radial extender means further includes a cam means engageable against said resilient support member when said push-bar means is moved to selectively extend and retract said probe means.

18. A system as defined in claim 17, wherein said tubular housing contains said resilient support member and said push-bar means, and wherein said cam means is mounted within said tubular housing.

19. A system as defined in claim 18, wherein said resilient support member includes a bent portion that slidingly engages said cam means when said push-bar means is moved to flex the probe means mounted on one end of said support member into a retracted position.

20. A system for remotely inspecting the interior walls of a metallic plug shell having an open end and a closed end that contains an expander element near its closed end which is provided with a centrally disposed bore, comprising:
an eddy current probe means having a distal end for engaging said cavity walls, and a proximal end;
an elongated support assembly operatively connected to the proximal end of the probe means that is insertable into and withdrawable from the open end of the plug shell and the bore of the expander element, including a radial extender means for selectively extending and selectively retracting the distal end of said probe means to avoid mechanical interference between said probe means and said expander element, and a tubular housing having an open end through which said probe means is extended out of and completely retracted into, and
a probe driving and delivery assembly for inserting the support assembly into the open end of the plug shell and through the bore of the expander element and for scanningly moving the probe means over the interior walls of the plug shell located between the expander element and the closed end of the plug shell.

21. A system as defined in claim 20, wherein said probe driving and delivery assembly includes a frame means, and a drive mechanism slidably mounted onto the frame means for driving the probe support assembly into the open end of the plug shell and through the bore of the expander element and for scanningly moving the probe means over the interior walls of the plug shell.

22. A system as defined in claim 21, wherein said drive mechanism includes a screw-threaded member for helically moving the probe means around the interior walls of the plug shell.

23. A system as defined in claim 21, wherein the drive mechanism includes an indexing means having a member insertable through the open end of the plug shell and engageable against the expander element to stop the sliding movement of the drive mechanism relative to the frame means to provide an indication of the location of the expander element within the plug shell.

24. A system as defined in claim 23, wherein said indexing member is a tubular member, and wherein the elongated support assembly is slidably movable within said tubular indexing member.

25. A system as defined in claim 23, wherein said support assembly, tubular indexing member and expander element each have a distal end, and wherein the distal end of the elongated support assembly is offset from the distal end of the tubular indexing member a distance equal to the length of the expander elements so that the distal end of the support assembly is even with the distal end of the expander element when said tubular indexing member engages said expander element.

26. A system as defined in claim 23, wherein the indexing means further includes a stand-off member mounted on the frame means that is engageable against the open end of the plug shell.

27. A system as defined in claim 26, wherein said stand-off means includes an opening for conducting both said indexing member and said probe support assembly.

28. A system as defined in claim 22, wherein said drive mechanism includes a reversible motor means, and a gear train for coupling the output of the motor means to the screw-threaded member.

29. A method for remotely inspecting the interior walls of a cavity within a metallic material that has a circular cross-section that has step-wise variations in radius by means of an apparatus having an eddy current probe means having a distal end for engaging said cavity walls, and a proximal end connected to an elongated support assembly having a housing for containing the eddy current probe means, and a radial extender means for selectively extending and retracting the distal end of the probe means from the longitudinal axis of the support assembly, comprising the steps of:
   inserting the support assembly into the cavity with the probe means completely retracted within said housing to avoid mechanical interference with the step-wise variations in the radius of the cavity walls, and
   extending the probe means into wiping engagement with the cavity walls while moving the support assembly in order to inspect said cavity walls.

30. A method for remotely inspecting the interior walls of a cavity as defined in claim 29, wherein said probe means is helically moved through said cavity with respect to the axis of rotation of said cavity.

31. A method for remotely inspecting the interior walls of a hollow metallic plug having a closed end and an open end and a circular cross-section that has been expanded by an expander element having a centrally disposed bore by means of an apparatus having an eddy current probe means with a distal end for engaging said cavity walls, and a proximal end connected to an elongated support assembly having a housing for containing the eddy current probe means, and a radial extender means for selectively extending and retracting the distal end of the probe means with respect to the housing, comprising the steps of:
   (a) retracting the probe means completely within the housing of the support assembly;
   (b) inserting the housing of the support assembly into the interior of the metallic plug and through the centrally disposed bore in the expander element until said probe means is disposed above said expander element, and
   (c) radially extending the probe means out of the housing and into engagement against the inner walls of the plug.

32. A method for remotely inspecting the, interior walls of a cavity as defined in claim 31, further comprising the step of helically moving the probe means within said plug above said expander element to inspect said plug.

33. A method for remotely inspecting the interior walls of a cavity as defined in claim 31, further comprising the step of determining the location of the expander element along the axis of rotation of the plug prior to radially extending the probe means to determine whether said expander element has properly expanded said plug.

34. A method for remotely inspecting the interior walls of a cavity as defined in claim 32, further comprising the steps of determining the location of the closed end of the plug, and ceasing the helical advancement of the probe means within said plug when said probe means confronts said closed end of said plug.

35. A method for remotely inspecting the interior walls of a cavity as defined in claim 34, further comprising the step of radially retracting the probe means completely into said housing after the advance of said probe means has ceased.

36. A method for remotely inspecting the interior walls of a cavity as defined in claim 35 further comprising the step of withdrawing the housing of the support assembly from the centrally disposed bore in the expander element and out of the interior of the plug.

* * * * *